United States Patent [19]
Pickett

[11] 3,939,019
[45] Feb. 17, 1976

[54] COVERING APPARATUS AND METHOD FOR FILM MOUNTED SERIAL TISSUE SECTIONS

[76] Inventor: John E. P. Pickett, 3323 Pinafore Drive, Durham, N.C. 27705

[22] Filed: Aug. 2, 1974

[21] Appl. No.: 494,064

[52] U.S. Cl. .............. 156/57; 156/192; 156/308; 428/906
[51] Int. Cl.². G01N 1/28; G02B 21/34; A01N 1/00
[58] Field of Search ....... 83/24, 915.5; 156/57, 276, 156/155, 280, 164, 301, 184, 302, 191, 303, 192, 310, 332, 314, 295, 324, 305, 459, 549, 495, 550, 547, 578, 307, 308; 117/3; 242/67.3 R, 67.4, 205; 118/325; 427/2; 428/906, 483

[56] References Cited
UNITED STATES PATENTS

| 1,516,506 | 11/1924 | Schultz | 156/310 |
| 1,944,835 | 1/1934 | Boyers | 117/111 F |
| 1,958,676 | 5/1934 | Peterson | 242/67.4 |
| 3,493,447 | 2/1970 | Rock | 156/57 |
| 3,498,860 | 3/1970 | Pickett | 156/57 |
| 3,673,037 | 6/1972 | Reavis | 156/299 |
| 3,677,860 | 7/1972 | Zychal | 156/301 |

*Primary Examiner*—Douglas J. Drummond
*Assistant Examiner*—J. J. Gallagher
*Attorney, Agent, or Firm*—B. B. Olive

[57] ABSTRACT

A covering apparatus and method is directed to applying transparent adhesive tape over stained serial tissue sections which have been mounted on motion picture type film. The tape serves as a protective cover for the sections in lieu of glass slides, plastic and glass cover slips, plastic sprays, and the like.

4 Claims, 4 Drawing Figures

COVERING APPARATUS AND METHOD FOR FILM MOUNTED SERIAL TISSUE SECTIONS

BACKGROUND OF THE INVENTION

1. Field of the Invention

The invention relates broadly to mounting of stained serial tissue sections for microscope observation but more specifically to an apparatus and method for covering film mounted tissue sections with transparent tape preparatory to microscope observation and subsequent storage and impregnating such sections during covering.

2. Description of the Prior Art

Stained histologic sections on glass slides are normally covered with thin cover glass. A synthetic adhesive is used when covering to adhere the cover glass and to keep the section clear for microscopic observation. When mounting the section on the glass slide, the stained section is kept moist with xylene until the synthetic adhesive is placed on and the cover glass is applied.

In 1954 when Cronar polyester film became available from E. I. duPont Company to serve as a base for motion picture film, the value of the Cronar film was seen for histologic sections due to being thin, e.g., .005 inch, flexible, clear, inert to staining solutions and heat resistant. The serial film-section procedure was worked out and beginning in 1956 Krylon clear acrylic spray plastic was used as a cover for the stained sections on 5-foot film lengths. After drying of the plastic coat, sections were observed under the microscope. The spray plastic was not adaptable to long 100-foot strips of film-sections as a cover. A thick Krylon base-plastic was obtained and a technique was worked out for dipping the stained film-sections in the thick plastic with the film-sections mounted on a stainless steel photographic developing reel. An automatic water bath for volume section cutting and film mounting was also developed. Reels of film-sections containing 100-foot lengths of film were later used and the mentioned thick Krylon plastic was used as a cover for the sections. However, histology technicians found it difficult to maintain the proper thickness of plastic on a continuous basis. Solvents used with the plastic were found to be toxic which required special ventilation such as a hood for discharging the fumes. Most tissue sections fall within 3 to 12 microns thickness. Section thickness was critically limited, however, to not more than 10 microns in the process just described. If the sections were more than 10 microns in thickness, the plastic would not cover the sections and under the microscope proper clarity was not obtainable. Also, uneven sections did not lend themselves to being covered by this technique.

An improvement upon the mounting methods and devices of the prior art is revealed in U.S. Pat. No. 3,552,247. This patent discloses mounting tissue sections directly onto a film base by a method and apparatus which eliminates the heretofore usual interim manual lifting of the cut sections from the blade and the usual water bath and manual floating steps. A microtome trough filled with a liquid receives the cut tissue sections directly from the microtome knife. The sections are floated across the trough and into contact with film which is passed through the trough.

Reference may be made to three publications of interest, namely: A.M.A. Archives of Pathology, March 1960, Vol. 69, pp. 239-247, "Thirty-Five MM. Film as Mounting Base and Plastic Spray as Cover Glass for Histologic Sections", John Phillip Pickett, H. T., and Joachim R. Sommer, M.D., Durham, North Carolina; Archives of Pathology, April 1964, Vol. 77, pp. 429-433, "Improved Film Strip Technique for the Laboratory", J. P. Pickett, H. T. (ASCP), W. B. Greene, N. T. (ASCP) and Joachim R. Sommer, M.D., Durham, North Carolina; and American Review of Respiratory Disease, Vol. 102, 1970, "SERIAL SECTIONS OF LUNG — The use of a 70-Millimeter Film-Strip Technique for Large Tissue Sections", James W. Wilson and John Phillip Pickett. Also, see U.S. Pat. No. 3,498,860 which may be of general interest and U.S. Reissue Pat. No. Re. 24,906 relating to an adhesive tape useful in the invention.

As further background to the invention, reference is made to the Vickers cytology screening apparatus which was developed in 1968 by Vickers Instruments of Croydon, England. Although the Vickers apparatus was apparently never successfully marketed, it is noted that one aspect of the apparatus deals with the adhesive tape covering of a line of previously unembedded cells which are singularly mounted on a plastic strip so as to form a continuous hairline on the strip. Although the singular cell line of the Vickers apparatus is mounted on a plastic strip prior to adhesive tape covering, the cells are not adhered to a polyester film as in tissue mounting and the cells to be covered have previously undergone neither paraffin embedding, serial microtome slicing, nor a staining process which additionally serves to remove the paraffin embedding material. Such process has not dealt with the matter of impregnating tissue sections with optically clear adhesive and covering with an optically clear tape using such adhesive.

Note is also taken of an apparatus previously marketed as the Cytotrack Trace Laying System by Tetronics Research and Development Company, Lechlade Road, Faringdon, Berkshire, England. As with the Vickers apparatus elsewhere described, the Tetronics apparatus is concerned with mounting of cells as distinct from tissue sections which is the subject of the present invention. In using the Tetronics apparatus, cells are placed in a container, mixed with fixatives and stains, and the cells are allowed to drop from the container onto a film in a thin, hairline width trace. After being mounted on the film, the cells are sealed with a transparent polymer in a manner somewhat akin to prior art spray covering techniques. While such an apparatus and method have apparently been used successfuly for fixing, staining, mounting, and covering cells, they are basically limited to those specific purposes because of the substantially different problems encountered with mounting, covering, and viewing the conventionally paraffin-embedded, larger, non-uniform tissue sections and with impregnating such sections.

The referred to prior art deals with both light and electron microscopy techniques and while the concept of mounting tissue sections serially on film and covering the film mounted sections with plastic are known and have been practiced, it can readily be seen and appreciated that an expanding medical industry requires substantial improvements in method and apparatus for covering film mounted serial tissue sections and impregnating for optical clarity.

SUMMARY OF THE INVENTION

The method and apparatus of the present invention is directed to the concept of covering extremely thin, i.e., 3 to 12 microns, tissue specimens which have previously undergone paraffin embedding, serial microtome slicing, serial film strip mounting, and a staining process which also acts to remove the paraffin embedding material from the film mounted tissue sections. Covering, according to the invention, involves adhering a transparent adhesive tape to the side of the film on which the sections are mounted. The merger of the film strip and the adhesive cover tape is assisted by the liberal application of a xylene-plastic solution to the adhesive side of the tape just prior to the point of merging. The xylene of the solution acts to slowly dissolve the adhesive without affecting the film or the base tape and the dissolved adhesive combines with the dissolved plastic of the solution to form an adhesive mixture which fills in the interstices of the tissue section previously occupied by the paraffin embedding material. Such impregnation or filling-in begins to occur as the solution wet side of the tape and the section mounted side of the film strip pass together through the merging rollers of the invention apparatus. Excess solution is wiped from the covered film strip which is then wrapped firmly onto a storage reel. When the entire length of film has been covered, wiped, and wrapped on the storage reel, it is left for about fifteen minutes during which the adhesive mixture impregnates the tissue section interstices and sets. The trailing end of the film is next led through a crimper and attached to the spiraled film supply reel and the covered film strip is rewound onto the spiraled reel. This loaded reel is then transferred to a 60°C oven for overnight drying of the covered film strip which ultimately produces an optically clear laminate.

Excellent quality is seen under the microscope with the resulting tape-film sections. Thicker than 10 micron sections, although the exception rather than the rule, can now be cut and placed on film to get the proper cover and uneven sections lay flat with adequate cover. An operation involving a time of 6 minutes is now required for covering 100 feet of film mounted sections or 3,000 sections. Heretofore, with thick plastic dipping, the same operation required approximately 3 days.

Other advantages of this invention will become apparent when the following detailed description is read in conjunction with the appended drawings and claims. A preferred embodiment of this invention will now be described with reference to the accompanying drawings.

DESCRIPTION OF THE PREFERRED EMBODIMENT

Figure 1:
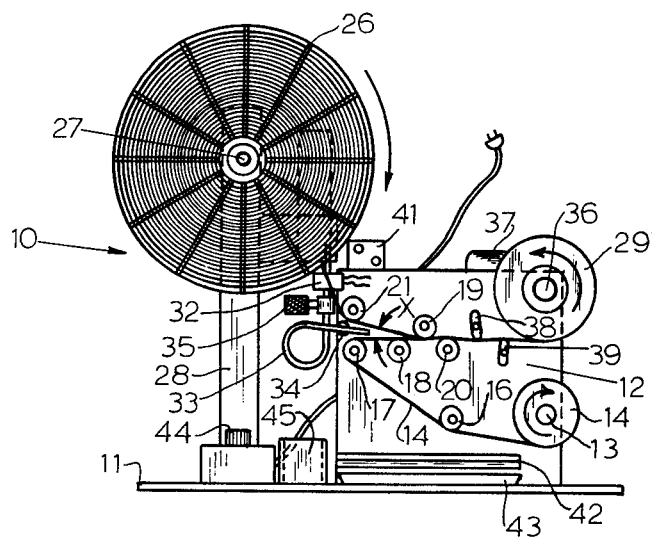
FIG. 1 is a front elevation view of the film covering tape apparatus of the present invention arranged for handling a 100-foot 35 mm film reel.
Figure 2:
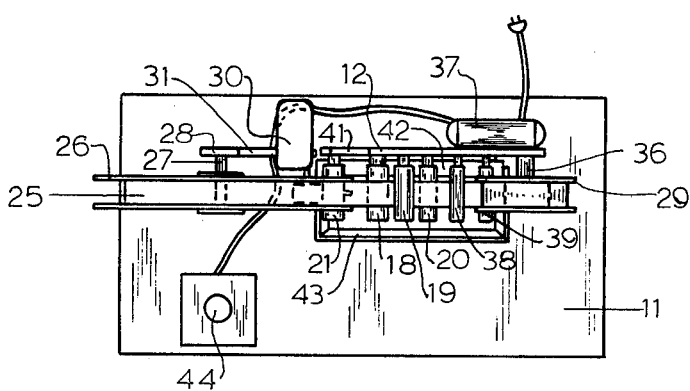
FIG. 2 is a plan view of the film covering tape apparatus of FIG. 1.

Referring to the drawings, there is illustrated a tape apparatus 10 for covering film mounted serial sections. Base 11 has an upright plate member 12 made integral with base 11 at a predetermined location thereon. Upright plate 12 has a shaft 13 fixedly secured adjacent base 11 at a predetermined height. Shaft 13 receives a roll of adhesive tape 15 from tape supply reel 14. Tape 15 is a pressure sensitive, transparent, acetate film tape and in a preferred embodiment is the type 800 tape manufactured under the brand name "Scotch" by 3M Company and is commercially available. It is otherwise described as an adhesive tape having a pressure-sensitive coating of acrylate ester copolymer and is marketed under U.S. Pat. No. Re. 24,906.

The type of adhesive tape used and its manner of merger with the film are critical to success of the invention. The base tape or tape backing must be optically transparent after the merger with the film. Equally important, the adhesive substance on the base tape must produce optical clarity after impregnating the tissue interstices and being set. The tape adhesive must also dissolve or at least be placed in a flowable state when combined with a solvent, e.g., xylene or heptane, and the dissolved adhesive must be compatible with the film, tissue and conventional stains in order to satisfactorily impregnate the tissue and set with optical clarity. Furthermore, since tissue sections are often stored for several years, the merged film-adhesive-base tape must provide a composite structure whose optical clarity remains after several years of storage. The mentioned 3M type 800 tape has been discovered as having all of the required qualities when applied as described and its unique properties were discovered only after diligent searching and trial of many methods and many types of adhesive tape-film-solvent-combinations. Tapes of a kind useful to the invention are more fully described in the previously mentioned U.S. Pat. No. Re. 24,906. From this description of the preferred adhesive tape and method of using such tape, it can also be seen that the choice of film on which the sections are mounted is also important to success. In this regard, it has been found that the well established use of Cronar polyester film lends itself in all respects to being adhered to the described type of adhesive tape in the manner of the invention.

Flanged guide rollers 16, 17, 18, 19, 20 and 21 are rotatably mounted on upright plate member 12 and are arranged so as to maintain tension upon film 25 and tape 15 as they are pulled through tape cover apparatus 10. A slight tension enhances the sealing between tape 15 and film 25 without damaging the tissue sections. A film supply reel 26 is rotatably mounted on shaft 27 which is in turn made integral with an upright reel support member 28. Reel 26 in one embodiment is a 35 mm, 100-foot length reel containing film 25 which is mounted with tissue sections that have previously been embedded in paraffin and sliced by a microtome before being mounted on film 25. It is also important to note that after the tissue sections are mounted on film 25 and before they are covered with the tape, they are exposed to a staining process which incorporates xylene. The tissue sections are thus stained and at the same time the paraffin embedding material is evacuated from the sections by means of the xylene which is used as a last step in conjunction with the staining process. As the mounted sections reach the covering apparatus of the invention, they are thus in the state of having been stained, of having had the embedding medium removed, of being approximately 3 to 12 microns in thickness and of having been adhered to one side of film 25. It is highly desirable that the mounted and stained serial tissue sections reach the covering apparatus in a wet state, i.e., wet from xylene used in the last states of staining. Otherwise, the sections are prone to separate from the film prior to mounting. Heptane and toluene operate like xylene.

Film 25 is fed from reel 26, beneath guide rollers 21 and 19 and then onto a storage reel 29. The side of film 25 on which the stained sections are mounted is guided toward the adhesive side of tape 15. Tape 15 is fed from tape supply reel 14, beneath flanged guide rollers 16, around flanged guide roller 17, over flanged guide roller 18, beneath flanged guide roller 19, over flanged guide roller 20 and on into storage reel 29. Tape 15 and film 25 come together and merge at a point just prior to their passing beneath flanged guide roller 19. Wiper bars 38, 39 are pivotally mounted and wipe any of the excess xylene-plastic solution from the merged film-tape prior to its reaching a storage reel 29. Bars 38, 39 should be smooth surfaced and may, e.g., be made of brass. A deflector plate 42 is integrally secured to upright plate member 12 so that any of the xylene-plastic solution wiped off by wiper bars 38, 39 is directed into a catch pan 43 which can be emptied as required. Storage reel 29 is mounted on shaft 36 which is turned by a variable speed electric motor 37, (1/5 h.p.) the driving means for the apparatus. A spring loaded washer, not shown, on reel shaft 27 brakes reel 26 and enables the film and tape to assume essentially the same tensions. As the tape covered film is pulled through apparatus 10 by motor 37, the tapefilm laminate is firmly rolled onto reel 29. Since a certain force is required to unroll the adhesive tape the motor 37 is adjusted to produce this force and this amount of force produces a satisfactory operating tension in both film and tape. The tape and film after merger should be rolled firmly but not tightly to avoid squeezing. A suitable control box allows for manual switching for speeding up, slowing down and start/stop operations for tape apparatus 10. (See box 44.) Just prior to the point of merger, tape 15 passes beneath supply line 33 from which a xylene-plastic solution flows onto the adhesive surface of tape 15.

A container 30, e.g., polyethylene, rests on a container support member 31 which is secured to reel support member 28. A solenoid valve 32 mounted below container 30 controls the supply of the xylene-plastic solution from container 30. A supply line 33 connected to solenoid 32 directs the xylene-plastic solution from container 30 onto the adhesive side of tape 15. This arrangement allows the solvent-plastic solution to flow by gravity onto the adhesive and for the solvent to contact and start dissolving the adhesive. A supply line support 34 positions line 33 and holds it in the proper downwardly angled position. Manual adjustment means 35 allows for adjustment of the flow of the xylene-plastic solution from container 30. The film and tape, of course, move at the same rate which in one embodiment is about 15 feet per minute for 35 mm film. Precise alignment and equal speeds are critical.

One factor of importance in the application concerns the manner of winding the merged tape and film in order to minimize wrinkling. In this regard, it may be noted that the film is substantially thicker than the tape. Therefore, the merged tape and film are fed to take-up reel 29 so that the tape is on the outside and the film on the inside of the spiral. Furthermore, when reeling the merged tape-film back onto reel 26 (FIG. 3) prior to drying it is also important that the tape be on the outside of the spiral to minimize wrinkling in the merged tape-film.

It has been found that a direct merger of any of the known types of transparent adhesive tapes with the type film described will not provide a covering which has the desired optical clarity. Such a direct merger of tape and film also lacks uniformity in its characteristics and its long-term durability in storage is questionable. Therefore, for a more practical merger of tape and film, it has been found that by adding at the point of merger a solvent, e.g., xylene, in which the adhesive substance on the adhesive tape is soluble; by further adding another substance, in a lesser amount, e.g., a liquid acrylic base plastic, which is also soluble and effectively supplements the amount of adhesive substance; by premixing and flowing this solvent-plastic solution in excess between the adhesive tape and film immediately prior to the point of merger; by immediately thereafter merging and pressing the tape and film together; and allowing them to remain for a short time, e.g., fifteen minutes, rolled on the take-up roll, the combined plastic and adhesive effectively penetrate the tissue and set and the solvent evaporates sufficient to allow handling of the film tape. Furthermore, by immediately wiping away the excess solvent as described below and subsequently drying the laminated film-tape as further described, the ultimate covered film has the desired characteristics of optical clarity, durability and adaptation to variations to thickness, characteristics which have not heretofore been achieved.

The xylene of the solution thus causes the adhesive on the tape to dissolve relatively slowly and mix with the dissolved plastic of the solution. Upon the merging of tape 15 and film 25 at guide roller 19, this mixture begins to penetrate the voids in the film mounted tissue sections previously occupied by the paraffin embedding material and removed by the staining process. The penetration continues and is effectively completed during the time, e.g., 15 minutes, the merged film and tape remain on the take-up reel 29. Also, by the end of this period, the adhesive substance has set so that the merged film-tape can be safely handled for drying.

Figure 3:
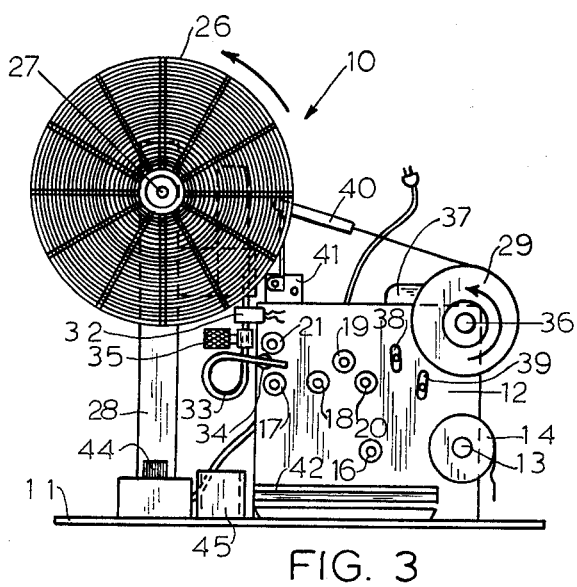
FIG. 3 is a front elevation view of the film covering tape apparatus of the present invention arranged for returning the tape covering film from the storage reel through a film crimper and back onto the original supply reel.

Once all of the film on supply reel 26 has been covered by tape 15 from tape supply reel 14 and has been guided onto storage reel 29, apparatus 10 is set up to transfer the tape covered film from storage roll 29 back to spiraled film supply reel 26, see FIG. 3. The tape covered film is preferably not allowed to remain on storage reel 29 for any long period of time while wet and in a rolled condition. 15 minutes time is deemed adequate. In order to manually transfer the film back to reel 26 from reel 29, reel 29 is remounted so that the tape side of the merged filmtape will be on the outside of the spiral as previously described. After this, the trailing end of the tape covered film is led through a conventional film crimper 40 which is pivotally mounted on crimper support 41. Crimper 40 places a slight curvature in the covered film as it passes from reel 29 through crimper 40 and back onto the spirals of reel 26. These spirals prevent the adjacent film surfaces from contacting each other during drying. As an alternative, the re-reeling operation could be motorized by the addition of a motor reversing mechanism to motor 37 and a drive belt connector means between motor 37 and shaft 27.

Figure 4:
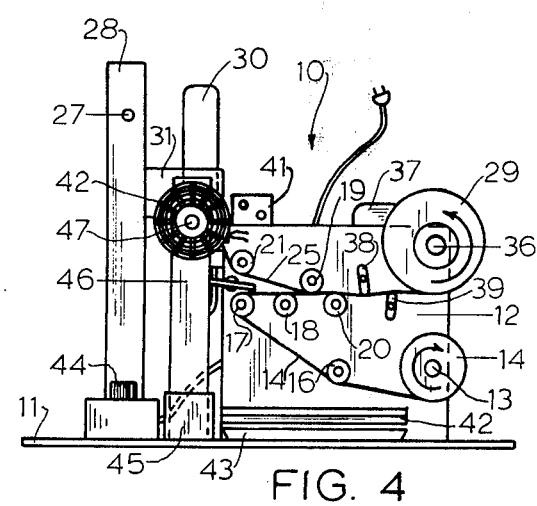
FIG. 4 is a front elevation view of the film covering tape apparatus of the present invention arranged for handling a 5-foot 35 mm film reel.

Referring to FIG. 4, tape apparatus 10 is set up to apply the tape covering of the present invention to a 70 mm, 10-foot strip of film mounted tissue. A small but wider supply reel 42 is used for supplying the 70 mm, 10-foot strip of film in the embodiment illustrated. A removable reel support 46 is positioned in support guide 45 and has an integral shaft 47 on which reel 42 rotatably mounts. The same procedure is carried out now for setting up of the film and for the covering process. Returning of tape covered film 25 to supply reel 42 from this smaller reel does not require use of crimper 40. In either case, when the re-reeling operation is complete, the reel is removed from the apparatus and placed in an oven at 60°C overnight. This causes the remaining xylene to evaporate leaving a transparent plasticadhesive bond between the film strip and the tape cover such that the tape covered film mounted tissue section strip is both durable and flexible, yet completely transparent and optically clear thereby affording excellent microscopic viewing.

From the foregoing description of the invention apparatus and method, it can be seen that the art is now provided with a practical means and method for impregnating with optically clear adhesive and covering substantial numbers of previously embedded and stained tissue sections simultaneouly. The long desired optical clarity and long term durability in relatively long length film mounted serial tissue have been achieved. Thus, when combined with the advanced film mounting techniques previously discussed, the art is now able to process substantial quantities of serial tissue sections in only a fraction of the time previously required.

It is contemplated that the usefulness of the invention apparatus and method will be primarily with film mounted sections on a strip of at least five feet in length, and where the section thicknesses are within a 3 to 12 micron range and normally in a 5 to 10 micron range. While xylene and an acrylic base plastic, as made and sold by the Sherwin-Williams Company, have been successfully employed as the wetting mixture (in the volume ratio 100 cc xylene, 900 cc plastic), heptane and toluene are also useful as solvents and a methacrylate base plastic as made and sold by duPont is also useful as a supplementary adhesive plastic. Various other mix ratios might be employed. A mixture that is too thick will cause the tape and film to separate in time whereas a mixture that is too thin prevents complete impregnation, leaves opaque voids and is otherwise unsatisfactory. At all times, the film and tape should be kept accurately aligned during merging and relative slippage must be avoided to prevent tissue damage. The included angle X (FIG. 1) at the merging position or station where the tape runs horizontally and the film downwardly angled should be a minimum acute angle. Sharp bending of the film at this or any other location should be avoided whether when spirally spaced as on the developing type film reel 26 or in the convolute roll on reel 29.

What is claimed is:

1. A method for impregnating with a substance which when dry is optically clear and covering with an optically clear cover serially mounted histologic tissue sections mounted on an optically clear film strip to prepare the sections for viewing and where the sections are in the state, following embedding, of having been sliced to a thickness within the 3–12 micron range, of having been serially adhered to one side of said strip, of having been stained and of having had the embedding medium removed from the tissue interstices, comprising the steps:

a. mounting on a film reel adapted for rotation a length of at least three feet of said film strip having serially mounted and adhered thereon a plurality of said 3–12 micron thick sections in said stained state;

b. rotatably mounting proximate said film reel a convolutely wound roll of adhesive tape in continuous tape form, said tape consisting of an optically transparent backing strip and on one side of said strip a coating of pressure sensitive adhesive substance characterized by being dissolvable in a selected solvent, in a dissolved state being adapted to impregnate the interstices of said stained tissue sections when submerged therein and in a dry state when confined in said interstices being optically clear;

c. pulling said tape and film from the respective roll and reel such that the side of said film mounting said sections and the side of said tape having said adhesive substance is guided to a station wherein said tape is maintained flat and horizontal during its travel and with said tape adhesive coated side disposed upwardly and at such said station said film is maintained flat and angled downwardly during its travel at an acute included angle with respect to the tape and with the mounted side of said film having the adhered serial sections disposed downwardly whereby to merge the entire surface of said tape adhesive coated side with the entire surface of said film mounted side and to thereafter bring the entire respective merged surfaces of the tape and film in a closely merged relation preparatory to being rolled into a coil;

d. providing at said station immediately prior to the place of said merger a flow of said selected solvent in which said tape adhesive substance is soluble, said solvent including a predetermined quantity of an additional adhesive substance dissolved therein, said amount of additional adhesive substance being selected to provide at the place of merger a flow of sufficient solvent over the entire surface of said tape coated side to combine with the tape adhesive thereon to insure such tape adhesive being sufficiently dissolved in a selected period of minutes to fully impregnate the interstices of said stained sections and with sufficient additional and compatible adhesive substance being supplied to insure said interstices being filled during the completion of said merger and following such merger to leave said stained sections optically clear;

e. taking up such merged film-tape in a convolutely wound roll at a predetermined speed and tension selected to allow said mixture of solvent and adhesive substance to cover said entire surface of said tape coated side prior to said merger and to allow said roll to be formed without damaging said sections;

f. after said merger allowing the merged tape film to rest in a firmly wound convolute form for a predetermined period of minutes to complete the impregnation of said sections by said dissolved adhesive substances and the setting of such substances;

g. after said period of minutes rewinding said merged tapefilm into a convolutely spaced reeled form for drying; and h. drying said merged tape-film while in said convolutely spaced relation to evaporate said solvent and complete the setting of said adhesive substances.

2. The method of claim 1 wherein said solvent is selected from the group consisting of xylene, toluene and heptane, said tape adhesive substance consists of a pressure sensitive adhesive coating of acrylate copolymer, and such amount of said additional adhesive substance as is employed is selected from the group consisting of an acrylic base and methacrylate base plastics.

3. The method of claim 1 wherein said state of said sections on said film strip prior to said impregnating and covering includes said sections being in a wet condition as received from the last stage of staining.

4. The method of claim 3 wherein said solvent is selected from the group consisting of xylene, toluene, and heptane, said tape adhesive substance consists of a pressure sensitive adhesive coating of acrylate ester copolymer, and such amount of said additional adhesive substance as is employed is selected from the group consisting of an acrylic base and methacrylate base plastics.

* * * * *

UNITED STATES PATENT OFFICE
CERTIFICATE OF CORRECTION

Patent No. 3,939,019            Dated February 17, 1976

Inventor(s) John E. P. Pickett

It is certified that error appears in the above-identified patent and that said Letters Patent are hereby corrected as shown below:

In the title, "APPARATUS AND" should be deleted per an amendment dated May 30, 1975.

Signed and Sealed this

Thirteenth Day of July 1976

[SEAL]

Attest:

RUTH C. MASON
*Attesting Officer*

C. MARSHALL DANN
*Commissioner of Patents and Trademarks*